United States Patent [19]

Felix

[11] 4,066,658
[45] Jan. 3, 1978

[54] RESOLUTION OF D,L-DEHYDROPROLINE

[75] Inventor: Arthur Martin Felix, West Caldwell, N.J.

[73] Assignee: Hoffmann-La Roche Inc., Nutley, N.J.

[21] Appl. No.: 603,404

[22] Filed: Aug. 11, 1975

[51] Int. Cl.$^2$ .......................................... C07D 207/22
[52] U.S. Cl. ............................ 260/326.2; 260/326.4; 260/DIG. 8
[58] Field of Search ....................... 260/326.2, DIG. 8

[56] References Cited

U.S. PATENT DOCUMENTS

| 2,794,025 | 5/1957 | Amiard et al. | 260/326.2 |
| 2,830,996 | 4/1958 | Vassel | 260/DIG. 8 |

FOREIGN PATENT DOCUMENTS

| 762,463 | 7/1967 | Canada | 260/326.2 |
| 1,102,096 | 10/1955 | France | 260/DIG. 8 |
| 785,012 | 10/1957 | United Kingdom | 260/DIG. 8 |

OTHER PUBLICATIONS

Felix et al., Int. J. Peptide Protein, Res 5, pp. 201–206 (1973).
Peacock et al., Wound Repair, pp. 196–198 (1976).
Robertson et al., J. Am. Chem. Soc. vol. 84, pp. 1697–1701 (1962).
Chuapil et al., Chem. Abs. vol. 81 : 75832d (1974).
Chuapil et al., Chem. Abs. vol. 80 : 118821y (1974).
Chuapil et al., Environ. Health Perspect. vol. 9, pp. 283–294 (1974).
Grant et al., New England Journal of Medicine, vol. 286, p. 194 (1972).
Kapoor; J. of Pharm. Sciences; vol. 59, pp. 1–27 (1970).
Robertson et al.; J. Am. Chem. Soc., vol. 84, pp. 1697–1701 (1962).

*Primary Examiner*—Donald G. Daus
*Assistant Examiner*—Mary C. Vaughn
*Attorney, Agent, or Firm*—Samuel S. Welt; George M. Gould

[57] ABSTRACT

D,L-3,4-dehydroproline is resolved in high optical yield by conversion to its N-protected derivative, treatment with R(+)alpha-methyl-p-nitrobenzylamine to form the diastereomeric salts, fractional crystallization, decomposition of the L-R salt and regeneration of the secondary amine group. The product L-3,4-dehydroproline obtained in extremely high optical purity is useful as an inhibitor of collagen synthesis.

6 Claims, No Drawings

RESOLUTION OF D,L-DEHYDROPROLINE

BACKGROUND OF THE INVENTION

Polypeptide compounds containing the 3,4-dehydroproline, particularly the L-3,4-dehydroproline residue have been found to be potent inhibitors of proline hydroxylase enzyme activity and thus 3,4-dehydroproline serves as a useful agent for the inhibition of collagen synthesis. Studies with radiolabelled D,L-3,4-dehydroproline is incorporated into collagen and total protein at one-fifth the rate observed for labelled L-3,4-dehydroproline. Moreover, it has been found that D-3,4-dehydroproline does not inhibit hydroxyproline formation while L-3,4-dehydroproline when added to a cell culture in an amount of 1 mM reduced intracellular [$^{14}$C]-hydroxyproline 40% and medium [$^{14}$C]-hydroxyproline 70%. It is clear from the foregoing that the L-antipode of 3,4-dehydroproline would be the therapeutic agent of choice for collagen inhibition. Thus a process for resolving D,L-3,4-dehydroproline to produce L-3,4-dehydroproline in high optical purity and yield would be of great importance.

Resolution of D,L-3,4-dehydroprolinamide has been achieved in the art using both enzymatic and chemical techniques. The enzymatic procedure involved use of hog kidney amidase and produced L-3,4-dehydroproline which contains at least 3% of the D isomer as determined by the manometric assay with D-amino acid oxidase. Attempts to obtain optically pure L-3,4-dehydroproline by fractional crystallization or by enzymatic destruction of the contaminating D-form failed. See Robertson and Witkop, J. Amer. Chem. Soc. 84, 1697 (1962).

These same researchers also resolved D,L-3,4-dehydroprolinamide chemically using ammonium (+)-alpha-bromocamphor-pi-sulfonate. However, the yield of the L-isomer obtained was poor and the optical purity of the product was variable and thus this procedure is not practical from a commercial viewpoint.

DESCRIPTION OF THE INVENTION

The present invention relates to an improved process for resolving D,L-3,4-dehydroproline to produce the desired L-isomer in high optical purity and good chemical yield. It has now been discovered that D,L-3,4-dehydroproline in the form of its N-protected derivative can be resolved utilizing R(+)alphamethyl-p-nitrobenzylamine as the resolving agent.

In the initial process step D,L-3,4-dehydroproline is reacted with a suitable N-protecting group. The suitability of the protecting group is determined by the conditions required for deblocking. These conditions must be such that no racemization occurs for the resolved protected compound.

Examples of suitable N-protecting groups include t-butyloxycarbonyl, formyl, trifluoroacetyl, and phthalyl. These groups may be introduced and removed employing procedures well known in the art. Thus the t-butyloxycarbonyl group is provided by reaction of t-butyloxycarbonyl azide in dioxane at pH 8.6 and at room temperature. Deblocking of this group is accomplished by treatment of the resolved protected compound with trifluoroacetic acid at room temperature in a chlorinated hydrocarbon solvent, i.e., methylene chloride. Alternatively, the deblocking may be carried out with formic acid (aqueous) preferably 85% formic acid at room temperature for 4 hours.

The formyl group is introduced by reacting the D,L-starting material with formic acid at 100° C. and subsequently removed by treatment with 0.1N alcoholic hydrogen chloride.

Attachment of the trifluoroacetyl group is accomplished by reaction with trifluoroacetic anhydride in trifluoroacetic acid at 0° C. while deprotection occurs on treatment with dilute ammonia solution.

Finally, fusion of the racemate with phthalic anhydride at a temperature of 150° C. serves to provide the phthalyl protecting group and removal of said group is conveniently accomplished by hydrazinolysis, i.e., by treatment at reflux with methanolic hydrazine for about 2 hours.

For the purposes of the present invention the t-butyloxycarbonyl protecting group is especially preferred.

Resolution of the N-protected D,L-3,4-dehydroproline is accomplished by forming the diastereomeric salt with R(+)alpha-methyl-p-nitrobenzyl amine. Salt formation is readily accomplished by treating the racemate in solution in a lower alkanol or lower alkyl ketone solvent either anhydrous or in the added presence of water, or with a solution of the resolving agent at room temperature (the reaction is slightly exothermic) followed by storage for 2 to 10 days at reduced temperature such as about 4° C. The resulting N-protected-L-3,4-dehydroproline(R)-alpha-methyl-p-nitrophenethylammonium salt precipitates from solution. For purposes of the present invention isopropanol is a lower alkanol of preference as solvent for the resolution step.

The resolving agents (R) and (S) alpha-methyl-p-nitrobenzylamine have been previously described in the literature. Thus Cope et al., Journal of the American Chemical Society, Vol. 92, page 1243 (1970) describe the use of the above antipodes as complexes with platinum in the partial resolution of a cyclic allene such as 1,2-cyclononadiene. More recently, U.S. Pat. No. 3,901,915 described the resolution of specific racemic organic carboxylic acids such as epoxyaconitic acid, hydroxycitric acid gamma lactone, N-benzoyl-6-chlorotryptophan and N-lower alkanoyl-6-chlorotryptophan using the subject resolving agents.

Treatment of the residue derived from the mother liquors of the aforesaid resolution step with S(−)alpha-methyl-p-nitrobenzylamine in analogous fashion provides the N-protected-D-3,4-dehydroproline (S)-alpha-methyl-p-nitrophenethylammonium salt.

The diastereomeric salts can be readily decomposed by treatment with cold aqueous weak acid. Suitable weak acids useful for this decomposition step include organic acids such as citric acid or acetic acid and inorganic acids such as phosphoric acid, boric acid and the like. Citric acid is a preferred organic acid for the decomposition.

Removal of the N-protecting group can then be carried out by procedures selected on the basis of the identity of the respective groups. Suitable conditions for the protective groups useful in the practice of the invention have been described above.

The precise determination of the optical purity for the antipodes of 3,4-dehydroproline can be accomplished by use of the procedure developed by Manning and Moore, J. Biol. Chem., 243, 5591 (1968). When the present process is utilized employing t-butyloxycarbonyl as the N-protecting group, L-3,4-dehydroproline in over 99% optical purity can be recovered in good chemical yield. Thus racemization during deblocking is seen not to be a problem in the instant process.

The D-3,4-dehydroproline and intermediates used in the preparation thereof according to the instant process are useful as intermediates in preparing L-3,4-dehydroproline as the members of the D series may be racemized by conventional techniques. i.e., by treatment with acetic acid/acetic anhydride and the racemate may be recycled through the present resolution process.

The term "lower alkanol" as used herein is meant to include straight or branched chain saturated alcohols having 1 to 6 carbon atoms such as methanol, ethanol, isopropanol, i-butanol and the like. The term "lower alkyl" as used herein includes straight or branched chain saturated hydrocarbon radicals having from 1 to 6 carbon atoms such as methyl, ethyl, isopropyl, n-pentyl and the like.

EXAMPLE 1

N-t-butyloxycarbonyl-DL-3,4-dehydroproline

Into a 2-liter 3-necked round-bottomed flask equipped with mechanical stirrer assembly, dropping flask, inlet tube and an electrode connected to an autotitrator (pH setting, 8.6), was placed DL-3,4-dehydroproline (39.55 g., 0.35 mol), in NaOH (350 ml.) and dioxane (175 ml). t-Butyloxycarbonyl azide (54.6 g., 0.385 mol) in dioxane (175 ml) was added dropwise with stirring (pH maintained at 8.6 by means of the autotitrator using 4 M NaOH as titrant) over a 1 hour period. The reaction mixture stirred for 14 hr. at 25° and evaporated to dryness at the rotary evaporator. The residue was taken up in water and extracted with ethyl acetate (three times). The organic layer was back-extracted with 1 M NaHCO$_3$ (twice), water (twice) and the combined aqueous layers cooled in ice and acidified to pH 5 with 1 M citric acid. It was extracted with ethyl acetate (four times) and the organic phase back-extracted with water (twice). The ethyl acetate layer was dried over MgSO$_4$, filtered, evaporated to dryness and crystallized from ethyl acetate-petroleum ether. A white crystalline product was obtained, yield 56.6g. (75.1%); m.p. 113°-115.5°.

Anal. Calcd. for C$_{10}$H$_{15}$NO$_4$: C, 56.32; H, 7.09; N, 6.57. Found: C, 56.38; H, 7.17; N, 6.53.

EXAMPLE 2

N-t-Butyloxycarbonyl-L-3,4-dehydroproline (R)-alpha-methyl-p-nitrophenethylammonium salt Into a 500 ml. round-bottomed flask was placed N-t-butyloxy-carbonyl-DL-3,4 -dehydroproline (56.6 g., 0.265 mol) in isopropanol (150 ml.) and a solution of R(+)-alpha-methyl-p-nitrobenzylamine (43.98 g., 0.256 mol) in isopropanol (30 ml.) was added. Some warming occurred and the solution was stored at 4° for 2 days. Filtration afforded a tacky solid (the filtrate was used in the next experiment for the preparation of the D-S salt) which was crystallized from isopropanol. A white crystalline product was obtained, yield 35.4 g. (70.4%); m.p. 136.5°-138.5°; [α]$_D^{25}$ −181.4° (C, 1.01; MeOH).

Anal. Calcd. for C$_{18}$H$_{25}$N$_3$O$_6$: C, 56.98; H, 6.64; N, 11.07. Found: C, 56.98; H, 6.76; N, 10.75.

The optical rotation and melting point were essentially unchanged on further crystallization.

EXAMPLE 3

N-t-Butyloxycarbonyl-D-3,4-dehydroproline (S)-alpha-methyl-p-nitrophenethylammonium salt The mother liquor from the preceding synthesis of the L-R salt was evaporated to dryness, taken up in 1 M citric acid and extracted with ethyl acetate (five times). The combined organic extract was back-extracted with saturated NaCl, water, dried over MgSO$_4$, filtered and evaporated to dryness. The residue was taken up in isopropanol (150 ml.) and S(−)alpha-methyl-p-nitrobenzylamine (42.19 g., 0.254 mol) in isopropanol (30 ml.) added and stored at 4° for 2 days. Filtration afforded a tacky solid which was recrystallized from isopropanol. A white crystalline product was obtained, yield 38.2 g. (75.8%); m.p., 136°-137.5°; [α]$_D^{25}$ + 182.6° (C, 0.954; MeOH).

Anal. Calcd. for C$_{18}$H$_{25}$N$_3$O$_6$: C, 56.98; H, 6.64; N, 11.07. Found: C, 56.77; H, 6.60; N, 11.00.

EXAMPLE 4

N-t-Butyloxycarbonyl-L-3,4-dehydroproline

The L-R salt prepared in Example 2 (32.2 g., 84.9 mmol) was taken up in cold 1 M citric acid (100 ml.) and NaCl added. The viscous solution was transferred to a separatory funnel and extracted five times with ethyl acetate. The combined ethyl acetate extract was extracted with saturated NaCl (three times), dried over MgSO$_4$, filtered and evaporated to dryness. The residue was crystallized from ethyl acetate-petroleum ether. A white crystalline product was obtained, yield 14.12 g. (78.1%). m.p. 94°-96.5°; [α]$_D^{25}$ −272.5° (C, 1.04; MeOH).

Anal. Calcd. for C$_{10}$H$_{15}$NO$_4$:C, 56.33; H, 7.09; N, 6.57. Found: C, 56.35; H, 7.12; N, 6.67.

EXAMPLE 5

N-t-Butyloxycarbonyl-D-3,4-dehydroproline

The D-S salt (23.1 g., 60.9 mmol) was extracted as described for the L-R salt and worked up in the same manner. Crystallization from ethyl acetate-petroleum ether afforded 11.0g. (84.8%) of white crystalline product, m.p. 94°-96.5°; [α]$_D^{25}$ +273.8°, (C, 0.991; MeOH).

Anal. calcd. for C$_{10}$H$_{15}$NO$_4$: C, 56.33; H, 7.09; N, 6.57. Found: C, 56.22; H, 7.21; N, 6.58.

EXAMPLE 6

L-3,4-Dehydroproline

Into a 250 ml. round-bottomed flask equipped with a drying tube was placed N-t-butyloxycarbonyl-L-3,4-dehydroproline (5.00 g., 23.4 mmol) and a solution of 100 ml. of trifluoroacetic acid in methylene chloride (1:1) added and stood at 25° for 1 hr., evaporated to dryness at the rotary evaporator and the residue evaporated from water (three times). It was taken up in 0.4 M pyridine acetate (pH 3.5) and eluted through a column (7.5 × 4.5 cm) of Dowex 50WX2 with 0.4 M pyridine acetate (pH 3.5). A volume of 200 ml. was collected, evaporated to dryness and crystallized from isopropanol-ether. White crystals were obtained, yield 1.4g. (52.6%); m.p. 238°-241° dec.; [α]$_D^{25}$ −396.0° (C, 1.035; H$_2$O ); [α]$_D^{25}$ −270.2° (C, 0.935; 5NHCl).

Anal. Calcd. for C$_5$H$_7$NO$_2$: C, 53.09; H, 6.24; N, 12.38. Found: C, 52.88; H, 6.22; N, 12.22.

EXAMPLE 7

D-3,4-Dehydroproline

The reaction was carried out exactly as described for the L-isomer in Example 6 using 5.00 g. (23.4 mmol) of N-t-butyloxycarbonyl-D-3,4-dehydroproline. Product was worked up as described previously in Example 6 and crystallized from isopropanol-ether to afford 1.45 g. (54.5%) of white crystals, m.p. 239.5°–241° dec.; $[\alpha]_D^{25}$ + 268.6° (C, 0.955; MeOH).

Anal. Calcd. for $C_5H_7NO_2$: C, 53.09; H, 6.24; N, 12.38. Found: C, 52.89; H, 6.34; N, 12.11.

EXAMPLE 8

Optical Purity Determination of L-3,4-dehydroproline. Reaction of 3,4-dehydroproline with L-alanine N-carboxyanhydride A sample of 3,4-dehydroproline (5.7 mg., 50.0 mol) was placed into a 10 ml. conical shaped test tube equipped with a ground glass stopper and 5.0 ml. of sodium borate buffer (pH 10.2, 0.45 M) was added. The clear solution was cooled to 0° in an ice bath. The test tube was removed from the ice bath and maintained at 0°–4° by means of jacketing the tube with crushed ice using a rubber sleeve. The tube was vigorously agitated using a vortex mixer, the stopper was removed, and L-alanine N-carboxyanhydride (6.3 mg., 55.0 μmol) added all at once while swirling at maximum speed. After 2.0 min., 1.0 M HCl (2.0 ml.) was added with stirring, the contents of the tube filtered into a 10.0 ml. volumetric flask and diluted to the mark with 0.01 M HCl [peptide content: ∼5.0 μmol/ml]. A portion of this solution was diluted with 0.01 M HCl [2.0 ml. to 10.0 ml; peptide content: ∼1.0 μmol/ml]. These two solutions were used directly in the next step for resolution on the amino acid analyzer [the concentrated solution was used for quantitative detection of the minor diasteriomer and the dilute solution for quantitative determination of the major diasteriomer].

EXAMPLE 9

Resolution of Diasteriomers on the Amino Acid Analyzer

Ninhydrin colorimetric analysis was performed on the Jeol 5AH analyzer. The above solution (0.8 ml.) was applied to the jacketed (50°) ion exchange column (15.0 × 0.8 cm) containing Joelco custom resin AR-15. The ninhydrin reaction mixture was prepared from reagent grade ninhydrin, sodium acetate buffer (pH 5.5, 4.0 M) and methyl cellosolve. The ninhydrin reagent contained 0.4 g. of stannous chloride per liter and was stored at 5°. The ninhydrin reaction bath was set at 95°. The analyzer was equipped with an electronic integrator (infotronics CRS-12 AB). The column was equilibriated and eluted with 9.2 M sodium citrate (pH 3.28). Under these conditions the reaction mixture was well resolved:

L-Alanyl-D-3,4-dehydroproline (45-46 min.)
L-Alanyl-L-3,4-dehydroproline (57.58 min.)

The ninhydrin color value of the L-D dipeptide is slightly lower than that of the L-L dipeptide. This difference is taken into account in the optical purity calculation by using operational color values of 1.00 and 1.25 for the L-D and L-L dipeptide, respectively.

$$\%\text{L-3,5-Dihydroproline} =$$

$$\frac{\frac{\text{L-L isomer}^a}{1.25}}{\frac{\text{L-L isomer}^a}{1.25} + \text{L-D isomer}^b \times 0.2} \times 100$$

$$\%\text{D-3,4-Dehydroproline} =$$

$$\frac{\text{L-D isomer}^b \times 0.2}{\text{L-D isomer}^b \times 0.2 + \frac{\text{L-L isomer}^a}{1.25}} \times 100$$

[a]Determined from calculation of peak area of the dilute solution (∼1.0 μmol/ml).
[b]Determined from calculation of peak area of the concentrated solution (∼5.0 μmol/ml.) This value is therefore multiplied by a factor of 0.2 as shown.

EXAMPLE 10

Into a 250 ml. round-bottomed flask equipped with a magnetic stirring assembly was placed N-t-butyloxycarbonyl-L-3,4-dehydroproline (3.0 g., 14.1 mmol). A solution of 100 ml. of 85% formic acid was added, and the clear colorless solution was left standing at 25° for 4 hours. It was evaporated to dryness at the rotary evaporator (T 35°) and the residue evaporated from water (three times), and taken up in water (5 ml.). Isopropanol was added to the warm cloud point. Crystallization occurred when the mixture was kept at 4°. A total of 1.417 g. (89.2%) of L-3,4-dehydroproline was obtained in two crops. Recrystallization from water-isopropanol-ether gave white needles, m.p. 246°–247.5° dec.; $[\alpha]_D^{25}$ −402.2° (C = 1.006, H₂O); and $[\alpha]_D^{25}$ −284.8° (C = 0.998, 5N HCl). Thin-layer chromatography revealed that the product was homogeneous in 5 different systems. System 1, Rf 0.44; System 5, Rf 0.45; System 6, Rf 0.64; System 7, Rf 0.33; System 8, Rf 0.31.

Anal. Calcd. for $C_5H_7NO_2$: C, 53,09; H, 6.24; N, 12.38.

Found: C, 52.91; H, 6.18, N, 12.28

A similar reaction was carried out on a larger scale using N-t-butyloxycarbonyl-L-3,4-dehydroproline (18.0 g., 84.6 mmol) and gave 8.74 g. (91.4%) of L-3,4-dehydroproline.

An identical reaction starting with N-t-butyloxycarbonyl-D-3,4-dehydroproline (18.0 g., 84.6 mmol) gave 8.98 g. (93.8%) of D-3,4-dehydroproline with m.p. 245.5°–246.5° d; $[\alpha]_D^{25}$ + 402.3° (C = .9888, H₂O); $[\alpha]_D^{25}$ + 278.3 (C = 0.989, 5N HCl). The product was homogeneous in 5 different thin-layer systems. System 1, Rf 0.47; System 5, Rf 0.50; System 6, Rf 0.64; System 7, Rf 0.33; System 8, Rf 0.30.

Thin-Layer Systems

System 1. (butanol/acetic acid/ethyl acetate/water; 1:1:1:1).
System 5. (butanol/acetic acid/water; 4:1:1).
System 6. (n-propanol/pyridine/water/acetic acid/ethyl acetate; 25:20:30:5:20).
System 7. (n-propanol/water; 7:3).
System 8. (ethanol/water; 7:3).

I claim:

1. A method for the preparation of L-3,4-dehydroproline comprising in combination the steps of:
   A. treating N-protected D,L-3,4-dehydroproline with R(+)-alpha-methyl-p-nitrobenzylamine so as to form the corresponding diastereomeric salt, the said N-protecting group being selected from conventional N-protecting groups which can be deblocked without racemization of the resolved compound;

B. selectively crystallizing the N-protected L-3,4-dehydroproline (R)-alpha-methyl-p-nitrophenethyl ammonium salt from solution;

C. decomposing the aforesaid diastereomeric salt with cold aqueous weak acid so as to produce N-protected-L-3,4-dehydroproline; and D. removing the N-protecting group under conditions which do not cause racemization thereby yielding L-3,4-dehydroproline.

2. The process of claim 1 wherein said N-protecting group is selected from t-butyloxycarbonyl, formyl, trifluoroacetyl and phthaloyl.

3. The process of claim 2 wherein said N-protecting group is t-butyloxycarbonyl and the deblocking is accomplished by treatment of the resolved protected compound with aqueous formic acid.

4. The process of claim 1 wherein the formation of the diastereomeric salt in step (A) is carried out in lower alkanol or lower alkyl ketone solvent.

5. The process of claim 4 wherein said solvent is isopropanol.

6. A method for the preparation of L-3,4-dehydroproline and D-3,4-dehydroproline comprising in combination the steps of:

A. treating N-protected D,L-3,4-dehydroproline with R(+)-alpha-methyl-p-nitrobenzylamine so as to form the corresponding diastereomeric salt, the said N-protecting group being selected from conventional N-protecting groups which can be deblocked without racemization of the resolved compound;

B. selectively crystallizing the N-protected L-3,4-dehydroproline-(R)-alpha-methyl-p-nitrophenethyl-ammonium salt from solution;

C. decomposing the aforesaid diastereomeric salt with cold weak aqueous organic acid so as to produce N-protected L-3,4-dehydroproline;

D. removing the N-protecting group under conditions which do not cause racemization thereby yielding L-3,4-dehydroproline;

E. treating the mother liquors from step (B) with S-(−)-alpha-methyl-p-nitrobenzylamine so as to produce N-protected D-3,4-dehydroproline-(S)-alpha-methyl-p-nitrophenethyl-ammonium salt;

F. decomposing the diastereomeric salt of step (E) with cold weak aqueous acid so as to produce N-protected D-3,4-dehydroproline; and G. removing the N-protecting group under conditions which do not cause racemization thereby yielding D-3,4-dehydroproline.

* * * * *